United States Patent [19]

Klingler et al.

[11] Patent Number: 5,399,201
[45] Date of Patent: Mar. 21, 1995

[54] PROCESS FOR PREPARING 1,2-5,6-DIACETONE-D-GLUCOSE

[75] Inventors: Franz D. Klingler, Griesheim; Albrecht Christmann, Ingelheim am Rhein, both of Germany

[73] Assignee: Boehringer Ingelheim KG, Ingelheim am Rhein, Germany

[21] Appl. No.: 107,388

[22] Filed: Aug. 16, 1993

[30] Foreign Application Priority Data

Aug. 14, 1992 [DE] Germany ............ 42 27 022.7

[51] Int. Cl.$^6$ ............ C07H 1/00; C07H 3/00; C08B 37/00
[52] U.S. Cl. ................ 127/42; 127/58; 536/1.11; 536/124
[58] Field of Search ............ 127/42, 58; 536/1.11, 536/124

[56] References Cited

U.S. PATENT DOCUMENTS

Re. 30,379  8/1980  Gordon ............ 536/4
3,723,412   3/1973  Hicks et al. ...... 260/210 R
3,939,145   2/1976  Gordon ............ 260/210 R Primary Examiner—Paul Lieberman
Assistant Examiner—Patricia L. Hailey
Attorney, Agent, or Firm—A. R. Stempel; M-E. M. Devlin

[57] ABSTRACT

The present invention relates to an improved process for preparing 1,2-5,6-diacetone-D-glucose from D-glucose and acetone.

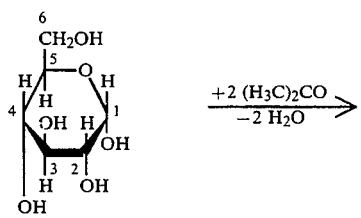

Alpha-D-glucopyranose

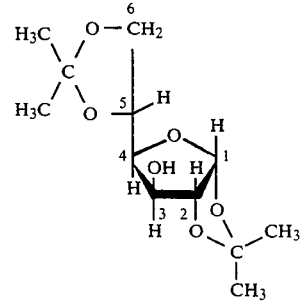

1,2:5,6-di-O-isopropylidene-alpha-D-glucofuranose

3 Claims, No Drawings

PROCESS FOR PREPARING 1,2-5,6-DIACETONE-D-GLUCOSE

The present invention relates to an improved process for preparing 1,2-5,6-diacetone-D-glucose (1,2:5,6-di-O-isopropylidene-α-D-glucofuranose)

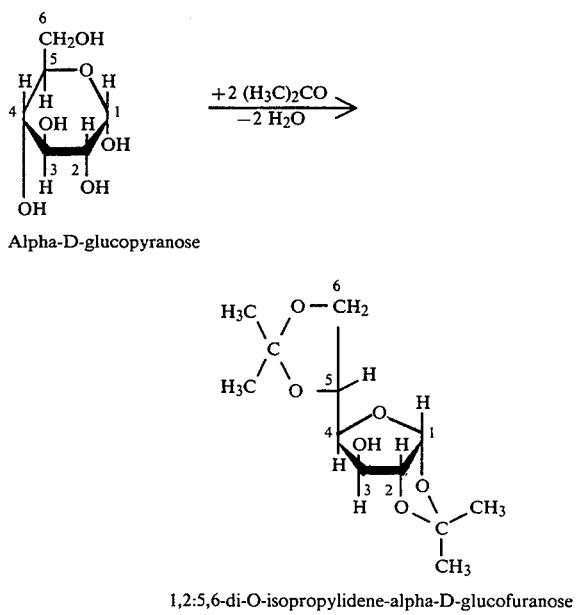

from D-glucose and acetone.

1,2-5,6-diacetone-D-glucose is a central intermediate product for numerous other glucose derivatives which are of great importance as drugs, inter alia. By way of example we will mention only 2-deoxy-D-riboseanilide and amiprilose.

In addition, 1,2-5,6-diacetone-D-glucose may be used as a chiral ligand in complexes which permit enantioselective reactions [F. D. Klingler and M. Psiorz, Chimicaoggi 1992, 47].

This central role of 1,2-5,6-diacetone-D-glucose is responsible for the fact that the annual requirement of this intermediate product is calculated in tons.

It is generally known from the prior art that monosaccharides which contain two sterically adjacent OH groups in the cis-position can be reacted with aldehydes or ketones in the presence of sulphuric acid, zinc chloride or phosphorus (V) oxide to obtain the corresponding acetals (E. Fischer, 1895).

Thus, 1,2:5,6-di-O-isopropylidene-α-D-glucofuranose (diacetone-α-D-glucose) can be obtained by reacting D-glucose with acetone in the presence of sulphuric acid. In order to achieve higher conversions, the water produced by the ketalisation must be bound or eliminated from the reaction mixture.

Other catalysts known from the prior art include iodine, gypsum or molecular sieves. However, the use of the catalysts which have hitherto been known to be suitable has serious attendant disadvantages—not only in terms of the reactions on an industrial scale—of which the following are mentioned by way of example:

when using inorganic acids or phosphorus pentoxide it is necessary to use large quantities of these agents, on the one hand resulting in a poor throughput and on the other hand causing serious problems of disposal of the salts produced by the neutralisation which is subsequently required;

if iodine is used large quantities of solvent are necessary, which again permit only a low throughput;

if an additional solvent is used which is capable of forming an azeotrope with water, the capacity of the reaction vessel has to be increased further, and in addition the use of an entraining agent such as pentane results in a lowering of the boiling point, thus limiting the reaction temperature and lengthening the reaction time accordingly;

the use of solid catalysts also presents problems because of the reactions of caramelisation which also take place, and moreover the reprocessing of ion exchangers involves very considerable expense;

in addition, many reactions have the disadvantage that the secondary reactions, the extent of which depends on the particular reaction conditions, e.g. the self-condensation of the acetone, produce tar-like by-products in certain cases which affect the efficacy of the catalyst, on the one hand, and lead to undesirable contamination of the reaction product, on the other hand, whilst some of these by-products can only be removed by chromatographic purification.

Thus, the process according to the invention makes it possible to prepare diacetone glucose in the presence of acidically reacting catalysts such as Lewis acids, preferably complex compounds of boron trifluoride, aluminium halides (such as aluminium(III)chloride), copper salts such as copper(II) chloride or bromide, iron salts such as iron(III) chloride or bromide, tin salts or halides of rare earths, the boron trifluoride-diethylether complex (boron trifluoride etherate) being particularly preferred (used in a quantity of 1% by weight based on the glucose put in), without the addition of dehydrating agents or other desiccant additives and without the addition of further solvents as entraining agents.

In order to perform the reaction the α-D-glucose is placed in a suitable autoclave and a mixture of acetone and boron trifluoride etherate is added. The reaction mixture is then heated until the pressure in the reaction vessel is at least 2.5 bar, preferably in the range from 2.5 to 10 bar and most preferably in the range from 2.5 to 5.5 bar. Then, at a temperature in the range from 80° to 130° C., preferably 85° to 120° C. and most preferably 88° to 115° C., the ingredients of the mixture which are volatile under these reaction conditions are distilled off, whilst acetone is added to the reaction mixture in proportion as the reaction medium distilled off is obtained as a distillate.

Distillation is continued until the quantity of distillate has reached at least 1⅔ times the original volume of acetone used. The reaction mixture remaining is then evaporated down to about half its original volume in vacuo at a temperature in the range from 30° to 70° C., preferably 35° to 50° C., and most preferably at a temperature of 40° C.

In the next reaction step the reaction mixture is diluted and stirred with the aqueous solution of a base, preferably an aqueous solution of an alkali metal hydroxide and most preferably with 2N sodium hydroxide solution and acetone.

The reaction mixture is then evaporated down once more in vacuo at a temperature in the range from 30° to 70° C., preferably 35° to 50° C. and most preferably at a temperature of 40° C., until all the organic components which are volatile under these conditions have been distilled off as far as possible. After cooling, the residue remaining is extracted with an organic extraction agent, preferably an aliphatic or aromatic hydrocarbon such as pentane, hexane, petroleum fractions, toluene or xylene, or an ether such as diethylether or methyl tert-.butylether, or a halogenated hydrocarbon, of which dichloromethane is particularly preferred.

The combined extracts are evaporated down in vacuo, the residue remaining is mixed with an organic filler or solvent, preferably an aliphatic hydrocarbon and more preferably cyclohexane and heated, under normal pressure, to a temperature in the range from 65° to 80° C., preferably to a temperature of 70° C., and then cooled to a temperature of about 10° C., the 1,2-5,6-diacetone-α-D-glucose being precipitated as a crystalline solid.

The crystals are then isolated and dried.

The objectives set out hereinbefore are achieved by means of the process described in the Examples. Various other embodiments of the process will become apparent to the person skilled in the art from the present specification. However, it is expressly pointed out that the Examples and associated description are intended only for the purposes of explanation and description and are not to be regarded as restricting the invention. In particular, it is pointed out that the synthesis sequence described in the Examples for preparing 1,2:5,6-di-O-isopropylidene-α-D-glucofuranose can also be applied to the preparation of other isopropylidene sugars.

The following monosaccharides are mentioned by way of example as starting materials which might be used: D-galactose, L- and D-arabinose, D-xylose, D-mannose, D-ribose, D-mannitol and L-ascorbic acid.

EXAMPLE 3.66 kg (20.32 mol) of anhydrous α-D-glucose are weighed into a reaction vessel flushed with protective gas and are then mixed with a mixture of 75 liters of acetone and 31 ml of boron trifluoride-diethylether complex. Under a pressure in the range from 1.6 to 4.4 bar, the ingredients of the reaction mixture which are volatile under these conditions in a temperature range of 88° to 115° C. are distilled off and acetone is added to the distillation residue at the rate at which the distillate is produced.

After a distillation time of 4 hours the supply of acetone is interrupted and 35 liters of acetone are distilled off under reduced pressure at a temperature of 40° C. Then the distillation residue is allowed to cool to ambient temperature and 3.1 liters of 2N sodium hydroxide solution and 19 liters of condensate are added.

The mixture is then stirred for a further 10 minutes and the acetone used is largely distilled out of the reaction mixture under reduced pressure (water ring pump vacuum). Then the distillation residue is allowed to cool to ambient temperature and 19 liters of dichloromethane are added and the mixture is vigorously stirred for 15 minutes. The extraction mixture is allowed to rest for 30 minutes and then the organic phase is separated off.

Extraction is repeated twice more using 13 liters of dichloromethane on each occasion and the combined extracts are then freed from extraction agent in vacuo. The residue is mixed with 22.5 liters of cyclohexane and heated to a temperature of 70° C. Then the solution is cooled to 10° C. and stirred at this temperature for 2 hours. The resulting crystal suspension is filtered and the crystalline residue is washed with cyclohexane and dried at a temperature of 40° C. under reduced pressure. In this way, 3.28 kg (62% of theory) of the 1,2:5,6-di-O-isopropylidene-α-D-glucofuranose are obtained in the form of a crystalline solid.

What is claimed is:

1. A process for preparing 1,2-5,6-diacetone-D-glucose which comprises reacting α-D-glucose in the presence of a Lewis acid selected from the group consisting of boron trifluoride, aluminium (III) halides, copper, iron and tin salts and halides of the rare earths with acetone at a temperature in the range from about 80° to about 120° C., under a pressure of at least about 2.5 bar, distilling off the volatile ingredients, and replacing the quantity of the distillate by acetone until about $1\frac{2}{3}$ times the original reaction volume has been substituted by acetone, evaporating down the reaction mixture at a temperature in the range from about 30° to about 70° C., mixing with an aqueous solution of a base, evaporating down the reaction mixture at a temperature in the range from about 30° to about 70° C., extracting with an organic extraction agent, evaporating down the extracts, combining the residue remaining after the evaporation with an organic sedimentation agent, heating to a temperature in the range from about 65° to about 80° C., cooling the resulting reaction mixture to a temperature of about 10° C. and isolating the crystals which are produced on cooling.

2. The process according to claim 1, characterized by reacting α-D-glucose in the presence of the Lewis acid with acetone at a temperature in the range from 85° to 120° C. under a pressure in the range from 2.5 to 10 bar, distilling off the ingredients which are volatile under these conditions and replacing the quantity of distillate by acetone until approximately $1\frac{2}{3}$ times the original reaction volume has been substituted by acetone, then evaporating down the reaction mixture at a temperature in the range from 35° to 50° C., mixing with an aqueous solution of an alkali metal hydroxide, evaporating down the reaction mixture at a temperature in the range from 35° to 50° C., extracting with an aliphatic or aromatic hydrocarbon or an ether or a halogenated hydrocarbon, evaporating down the extracts combining the residue remaining with a hydrocarbon, heating to a temperature in the range from 65° to 80°, cooling the resulting reaction mixture to a temperature of about 10° C. and isolating the crystals which are formed during cooling.

3. The process according to claim 2, characterized by reacting α-D-glucose in the presence of the Lewis acid boron trifluoride etherate with acetone at a temperature in the range from 88° to 115° C. under a pressure in the range from 2.5 to 5.5 bar, distilling off the ingredients which are volatile under these conditions and replacing the quantity of distillate by acetone until approximately $1\frac{2}{3}$ times the original reaction volume has been substituted by acetone, then evaporating down the reaction mixture at a temperature in the vicinity of 40° C., combining with 2N sodium hydroxide solution, evaporating down the reaction mixture at a temperature in the vicinity of 40° C., then extracting with a dichloromethane, evaporating down the extracts mixing the residue remaining with cyclohexane, heating to a temperature in the vicinity of 70° C., then cooling the resulting reaction mixture to about 10° C. and, isolating the crystals formed during cooling.

* * * * *